United States Patent [19]

Saiki et al.

[11] Patent Number: 4,683,194
[45] Date of Patent: Jul. 28, 1987

[54] METHOD FOR DETECTION OF POLYMORPHIC RESTRICTION SITES AND NUCLEIC ACID SEQUENCES

[75] Inventors: Randall K. Saiki, Richmond; Henry A. Erlich, Oakland, both of Calif.

[73] Assignee: Cetus Corporation, Emeryville, Calif.

[21] Appl. No.: 716,982

[22] Filed: Mar. 28, 1985

Related U.S. Application Data

[63] Continuation-in-part of Ser. No. 614,957, May 29, 1984, abandoned.

[51] Int. Cl.$^4$ .................. C12Q 1/68; C12N 15/00; C12P 19/34
[52] U.S. Cl. .................. 435/6; 935/78; 935/9; 436/811; 436/808; 435/91; 435/803; 435/810
[58] Field of Search .................. 435/6-8, 435/18, 28, 91, 267, 270, 803, 810; 436/63, 94, 501, 808, 811, 825, 504; 935/77, 78, 6, 9, 19, 86

[56] References Cited

U.S. PATENT DOCUMENTS 4,395,486  7/1983  Wilson et al. .................. 435/6
4,477,577  10/1984  Nakamura .................. 436/817 X
4,535,058  8/1985  Weinberg .................. 436/813 X

FOREIGN PATENT DOCUMENTS 0142299  5/1985  European Pat. Off. .

OTHER PUBLICATIONS

Wilson, J. T., et al. *Proc. Nat'l. Acad. Sci. USA*, vol. 79, 1982, pp. 3628-3631.
Boehm, C. D., *N. Engl. J. Med.*, vol. 18, 1983, pp. 1054-1058.
Lawn, R. M. et al., *Cell*, vol. 15, 1978, pp. 1157-1174.
Langer, P. R., et al., *Proc. Nat'l. Acad. Sci. USA*, vol. 78, No. 11, 1981, pp. 6633-6637.
Kan, Y. W. et al., *PNAS* (1978) 75:5631-5635.
Geever, R. F. et al., *PNAS* (1981) 78:5081-5085.
Orkin, S. H. et al., *N. Engl. J. Med.* (1982) 307:32-36.
Conner, B. J. et al., *PNAS* (1983) 80:278-282.
Kidd, V. J. et al., *Nature* (1983) 304:230-234.
Law, D. J. et al., *Gene*, 28 (1984) 153-158.
Phillips, J. A. III et al., *PNAS USA* (1980) 77:2853-2856.
Chang et al., *N. Eng. J. Med.* (1982) 307:30-32.

Primary Examiner—Esther M. Kepplinger
Assistant Examiner—Jeremy M. Jay
Attorney, Agent, or Firm—Janet E. Hasak; Albert P. Halluin

[57] ABSTRACT

In a method for detecting the presence or absence of a specific restriction site in a nucleic acid sequence an oligonucleotide probe complementary to one strand of the nucleic acid sequence spanning said restriction site is synthesized. The probe is labeled at the end nearer the restriction site. The nucleic acid is hybridized to the probe and a blocking oligomer may be added, if necessary, to prevent non-specific binding of the probe. Subsequent digestion with a restriction enzyme cleaves those oligomers that have hybridized to the nucleic acid and reformed the restriction site. The resulting cut and uncut labeled oligomers are separated and detected based on the type of probe label.

The described method may be used to detect sickle cell anemia.

28 Claims, 14 Drawing Figures

FIG.1

Specific 40 Base Length Oligodeoxyribonucleotide Probe HE09 And Complementary Blocking Oligomer HE10 Containing The Base Pair Mismatch Probe HE09        3' TTGGAGTTTGTCTGTGGTACCACGTGGACTGAGGACTCCT 5'

Blocking Oligomer HE10    5' AACCTCAAACAGACACCATGGTGCACCTGACTCCTGTGGA 3'
                                                              x x = Base Pair Mismatch

FIG. 2

Normal β-Globin
Specific Probe HE09:

5' AACCTCAAACAGACACCATGGTGCACCTGACTCCTGAGGAGAAGTCTGCC 3'
3' TTGGAGTTTGTCTGTGGTACCACGTGGACTGAGGACTCCT* 5'

↓ Digestion With DdeI

Normal β-Globin
Specific Probe HE09:

AACCTCAAACAGACACCATGGTGCACCTGACTCC    TGAGGAGAAGTCTGCC
TTGGAGTTTGTCTGTGGTACCACGTGGACTGAGGACT    CCT*

[3-mer*]

Sickle Cell β-Globin
Specific Probe HE09:

5' AACCTCAAACAGACACCATGGTGCACCTGAC—x—TCCTGTGGAGAAGTCTGCC 3'
3' TTGGAGTTTGTCTGTGGTACCACGTGGAC—x—TGAGGACTCCT* 5'

↓ Digestion With DdeI

Sickle Cell β-Globin
Specific Probe HE09:

AACCTCAAACAGACACCATGGTGCACCTGAC—x—TCCTGTGGAGAAGTCTGCC
TTGGAGTTTGTCTGTGGTACCACGTGGAC—x—TGAGGACTCCT*

[40-Mer*]

\* = Labeled Tag
x = Base Pair Mismatch

FIG. 3

Comparison Of The Normal β-Globin (β^A), Sickle Cell β-Globin (β^S) And Normal δ-Globin Sequences In The Region Of The Sickle Mutation

```
                             5'              x                    x                        x    3'
Normal β-Globin (β^A):   AACCTCAAACAGACACCATGGTGCACCTGACTCCTGAGGAGAAGTCTGCC Sickle β-Globin (β^S):   AACCTCAAACAGACACCATGGTGCACCTGACTCCTGTGGAGAAGTCTGCC Normal δ-Globin:         AACCTCAAACAGACACCATGGTGCATCTGACTCCTGAGGAGAAGACTGCT
                                                 /////
``` x = Base Pair Differences Relative to β^A

___ = DdeI Site (CTNAG)

///// = SfaNI Site (GCATC)

FIG.4

Effect Of Treating Genomic DNA With Restriction Enzyme
<u>SfaNI</u> Prior to Annealing To Specific Probe HE09

Normal β-Globin (β^A):
Specific Probe HE09:

```
AACCTCAAACAGACACCATGGTGCACCTGACTCCTGAGGAGAAGTCTGCC
TTGGAGTTTGTCTGTGGTACCACGTGGACTGAGGACTCCT*
```

Sickle
Cell β-Globin (β^S):
Specific Probe HE09:

```
                              —x—                    3'
     5'  AACCTCAAACAGACACCATGGTGCACCTGACTCCTGTGGAGAAGTCTGCC
         TTGGAGTTTGTCTGTGGTACCACGTGGACTGAGGACTCCT*
```

Normal δ-Globin (δ):
Specific Probe HE09:

```
                    x
AACCTCAAACAGACACCATGGTGCATCTGACT
TTGGAGTTTGTCTGTGGTACCACGTGGACTGAGGACTCCT*
```

Subsequent digestion with <u>DdeI</u> will result in the formation of a labeled 3-mer only when
the specific probe anneals to the normal β-globin gene.

x = Base Pair Mismatch

* = Label

FIG.5
1  2  3    4  5  6
TRIMER:
40-MER.
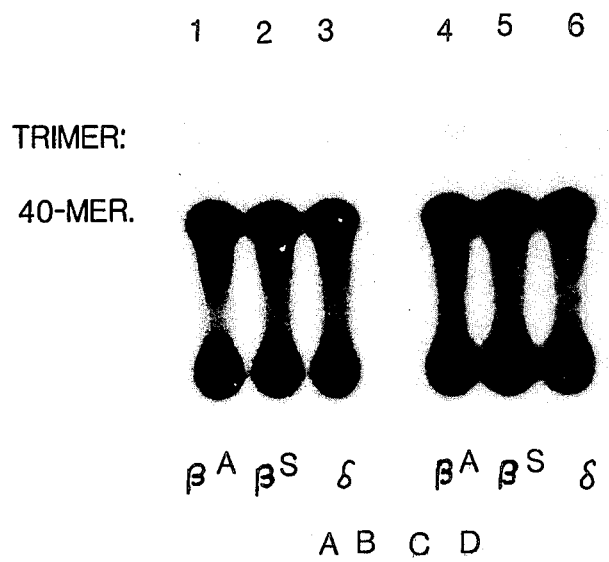
β^A  β^S  δ    β^A  β^S  δ
A  B  C  D
8-MER
3-MER
FIG.14

FIG. 7

β-Globin

```
HE09     :       3' TTGGAGTTTGTCTGTGGTACCACGTAGACTGAGGACTCCT 5'
                    ||||||||||||||||||||||||||||||||||||||||
beta(+)  :    5' GTTCACTAGCAACCTCAAACAGACACCATGGTGCACCTGACTCCTGAGGAGAAGTCTGCCGTTACTGCCCTGTGGGGCAAGGTGAACGTGG 3'
beta(-)  :    3' CAAGTGATCGTTGGAGTTTGTCTGTGGTACCACGTGGACTGAGGACTCCTCTTCAGACGGCAATGACGGGACACCCCGTTCCACTTGCACC 5'
                                                                 |||||||||||||||||||||||||||||
HE11     :                                                 5' TCCTGAGGAGAAGTCTGCCGTTACTGCCCTGTGGGGCAAG 3'
```

δ-Globin

```
HE09       :       3' TTGGAGTTTGTCTGTGGTACCACGTAGACTGAGGACTCCT 5'
                      ||||||||||||||||||||||||||||||||||||||||
delta(+)   :    5' GTTCACTAGCAACCTCAAACAGACACCATGGTGCATCTGACTCCTGAGGAGAAGACTGCTGTCAATGCCCTGTGGGCAAAGTGAACGTGG 3'
delta(-)   :    3' CAAGTGATCGTTGGAGTTTGTCTGTGGTACCACGTAGACTGAGGACTCCTCTTCTGACGACAGTTACGGGACACCCGTTTCACTTGCACC 5'
                                                                  |||| |||||||||||||||||||||||
HE11       :                                                5' TCCTGAGGAGAAGTCTGCCGTTACTGCCCTGTGGGGCAAG 3'

HE11       :    5' TCCTGAGGAGAAGTCTGCCGTTACTGCCCTGTGGGCAAG 3'
                   ||| ||||||||||||||||||||||||||||||||||||
HE12       :    3' AGGTCTCCTCTTCAGACGGCAATGACGGGACACCCCGTTC 5'
```

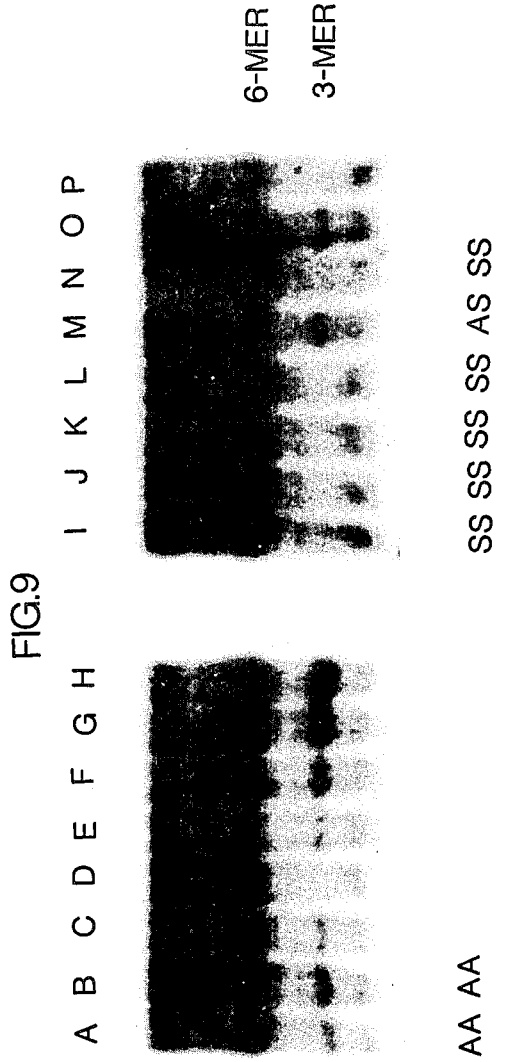

FIG. 10

```
           ==========----
β^A    CA TGG TGCACC TGAC TCC TGAGGAGAAG TC TGCCG TTAC TGCCC TG TGGGGCAAGG TGAA
       G TACCACG TGGAC TGAGGAC TCC TC TTCAGACGGCAA TGACGGGACACCCCG TTCCAC TT
           ==========----
```

```
                    =====   *
β^S    CA TGG TGCACC TGAC TCC TG TGGAGAAG TC TGCCG TTAC TGCCC TG TGGGGCAAGG TGAA
       G TACCACG TGGAC TGAGGACACC TC TTCAGACGGCAA TGACGGGACACCCCG TTCCAC TT
                    =====
```

\* Marks the mutation (A to T) in the sickle cell gene which disrupts the <u>Dde</u>I site

FIG. 11

```
RS06:   5'  *C TGAC TCC TGAGGAGAAG TC TGCCG TTAC TGCCC TG TGGG         3'
HE11:   5'       *TCC TGAGGAGAAG TC TGCCG TTAC TGCCC TG TGGGGCAAG      3'
```

```
                ==========----
RS06:           *C TGAC TCC TGAGGAGAAG TC TGCCG TTAC TGCCC TG TGGG
                |||||||||||||||||||||||||||||||||||||||||||||||
β(-):      G TACCACG TGGAC TGAGGAC TCC TC TTCAGACGGCAA TGACGGGACACCCCG TTCCAC TT
                ==========----
```

```
RS06:   5'  *C TGAC TCC TGAGGAGAAG TC TGCCG TTAC TGCCC TG TGGG          3'
            ||| |||| |  ||||||||||||||||||||||||||||||||||
RS10:   3'   GACAGAGG TCACC TC TTCAGACGGCAA TGACGGGACACCC               5'
```

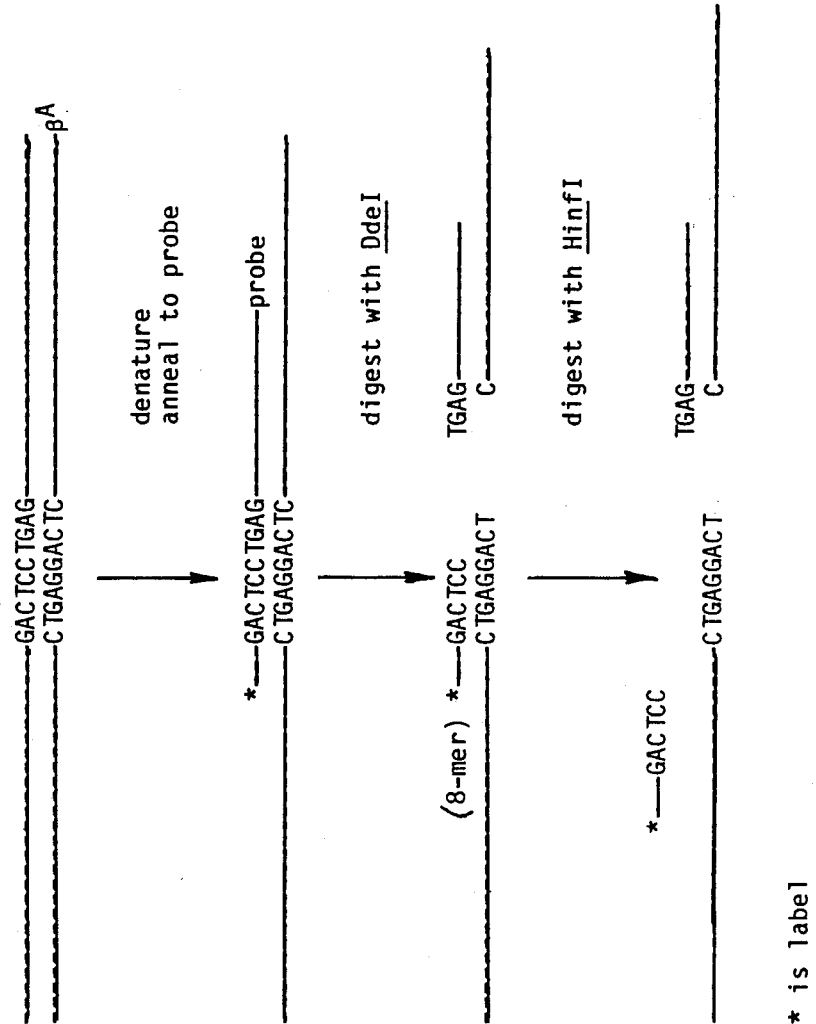

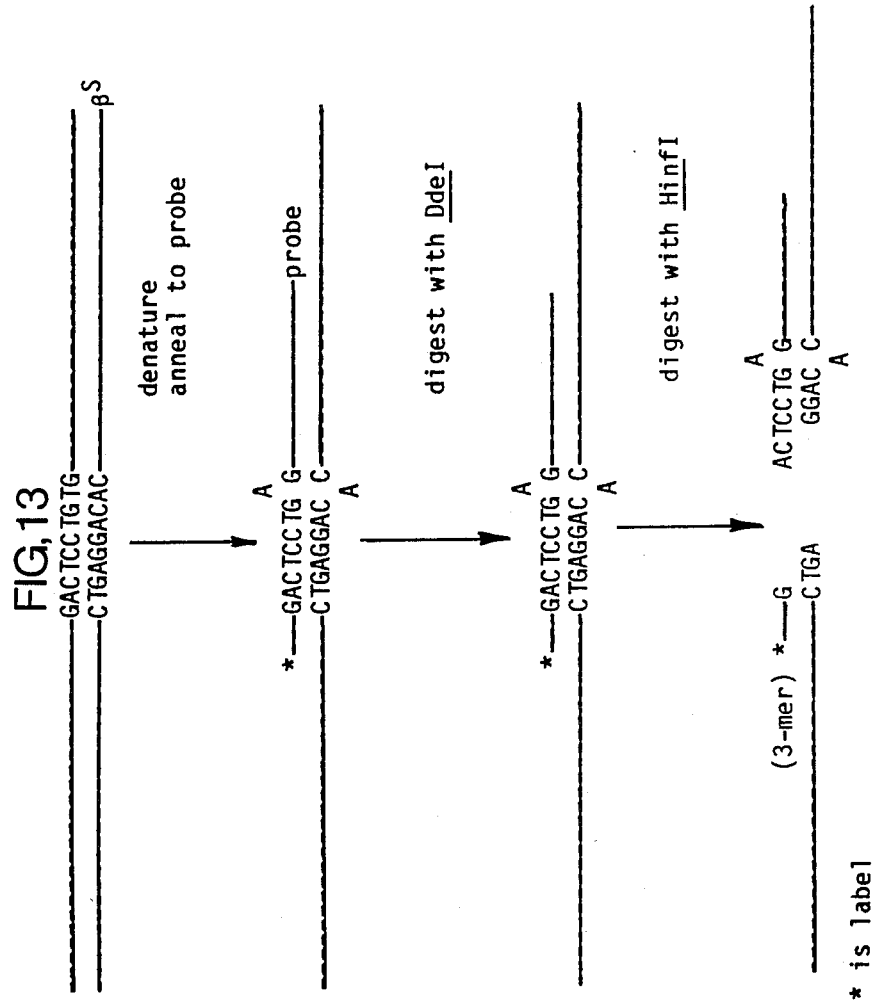

METHOD FOR DETECTION OF POLYMORPHIC RESTRICTION SITES AND NUCLEIC ACID SEQUENCES

This application is a continuation-in-part application of copending U.S. Ser. No. 614,957, filed May 29, 1984, now abandoned.

BACKGROUND OF THE INVENTION

This invention relates to the detection of the presence or absence of specific restriction sites in specific nucleic acid sequences using restriction endonculease cleavage of an end-labeled oligonucleotide probe annealed to the sequence spanning the site(s). An example of the use of this detection system is a method and test kit wherein an oligonucleotide probe is used for the direct analysis of human β-globin genes in the detection of sickle cell anemia.

In recent years the study of the molecular basis of hemoglobinopathies has made major advancements. Using sickle cell anemia and β-thalassemia as the model systems, researchers have attempted to understand more fully the molecular basis for these genetic diseases and to develop direct means of prenatal diagnosis.

Prior to 1981, work in this area centered on the study of restriction fragment length polymorphisms (RFLP). Researchers found that cleavage of the nucleotide sequences using site-specific restriction endonucleases yielded DNA fragments of defined length. Kan and Dozy, PNAS (1978) 75:5631–5635 reported RFLP's produced by HpaI cleavage of human β-globin genes, indicating a correlation between the 13.0 kb variant of the normal 7.6 kb fragment and the sickle cell mutation. This method of linkage analysis, though very useful, requires analysis of family members and even then is frequently unable to distinguish between normal and mutant genes. Because linkage analysis is based on the cosegregation of RFLP's associated with a specific disease within a family, the analysis is limited or inconclusive in cases where family studies are incomplete or unavailable.

In 1981, Geever, et al., PNAS (1981) 78:5081–5085 first reported a direct means for diagnosing sickle cell anemia which did not rely upon linkage analysis. This represented a major improvement in the diagnostic methods available since family studies would no longer be required in order to complete the analysis. Geever, et al. reported the use of a restriction endonuclease DdeI which recognizes the nucleotide base sequence "CTNAG" (where N is any base) for direct analysis of sickle cell anemia. The DdeI recognition site is abolished by the mutation (A to T) in the sickle cell allele of the β-globin gene. The results of this research indicated that use of such a specific endonuclease will result in the formation of restriction fragments varied in length dependent upon whether the mutation causing sickle cell anemia is present. A detailed description of the methods used by Geever, et al. for this direct analysis for sickel cell anemia is found in U.S. Pat. No. 4,395,486 issued July 26, 1983.

An improvement in the method of Geever, et al, is described by Orkin, et al., N. Engl. J. Med. (1982) 307: 32–36. The method differs from Geever, et al. in the use of a restriction enzyme MstII which also cleaves normal DNA but not sickle cell DNA. MstII generates larger fragments than those obtained with DdeI, and use of MstII eliminates some of the limitations present in the Geever, et al. method. Specifically, the modification by Orkin, et al. allows for the direct analysis of the sickle cell gene without the necessity of identifying the small DNA fragments resulting from digestion with DdeI. Further, it enables direct analysis of cells obtained directly from uncultured amniotic fluid.

Additional improvements on the method of direct analysis of sickle cell anemia are described by Conner, et al., PNAS (1983) 80: 278–282. In this article, a general method for the diagnosis of any genetic disease which involves a point mutation in the DNA sequence is described. The model system tested is the β-globin gene associated with sickle cell anemia; however, other similar methods (Nature (1983), 304: 230–234) have been used for prenatal diagnosis of α1-antitrypsin deficiency. The techniques as applied to both sickle cell anemia and α1-antitrypsin employ to use of a 19 base length oligodeoxyribonucleotide probe (19-mer). In the analysis of sickle cell anemia using the Conner et al. method, distinguishing between the normal β-globin gene and the sickle cell mutant requires specific probes approximately 19 bases in length and containing the single point mutation. This method is especially useful in the detection of α1-antitrypsin deficiency, since such a deficiency cannot be readily diagnosed by RFLP due to lack of restriction enzymes that yield clinically informative polymorphic patterns.

A drawback to the Conner, et al. method is the limitation inherent in using a 19 base oligomer probe. The distinction between the allelic variants is based on the thermal stability of the duplex formed between the genomic DNA and the synthetic oligodeoxyribonucleotide (19-mer) probe. Oligodeoxyribonucleotides much larger than the 19 base oligomer will not be sufficiently destabilized by a single base mismatch and so this approach cannot utilize probes substantially longer than 19 bases. However, given the complexity of genomic DNA, a 19-mer probe will hybridize to many DNA sequences in addition to the specific β-globin DNA sequence. This problem necessitates a gel electrophoretic step in which the β-globin fragment produced by digestion with a restriction endonuclease is separated from all the other fragments which hybridize to the probe. This step is essential in physically separating the "signal" (β-globin) from the "noise".

Once the fragments have been separated, the gel is dried followed by "in situ" hybridization of the probe to the electrophoretically separated fragments. Such manipulations of the gel are time consuming and present a technically difficult method of analysis.

As discussed, the references cited describe a direct method for the detection of genetic diseases using restriction fragment length polymorphisms (RFLP) or differential hybridization; however, they are limited in their applicability to routine clinical testing because of the complexity and sophistication required to carry out the analysis. The present invention overcomes these limitations by describing a fast yet sensitive method for detecting the presence or absence of specific polymorphic (as well as non-polymorphic) restriction sites. The method can be applied to genetic disorders capable of prenatal diagnosis such as sickle cell anemia or other genetic disorders where a polymorphic restriction site is clinically informative.

SUMMARY OF THE INVENTION

The present invention overcomes the disadvantages associated with the techniques discussed above by introducing a method for detecting the presence or absence of a specific restriction site in a specific nucleic acid sequence, through the use of specially designed oligonucleotide probes.

One embodiment of the present invention relates to a method for detecting the presence or absence of at least one specific restriction site in a specific nucleic acid sequence comprising the steps of:

(a) hybridizing said nucleic acid sequence with an oligonucleotide probe for each restriction site being detected which probe is complementary to a region in said nucleic acid sequence spanning the respective restriction site of the probe and which probe is labeled at the end nearer said respective restriction site;

(b) digesting said hybridized nucleic acid sequence with a restriction endonuclease for each probe which is capable of cleaving its respective probe at said restriction site being detected so as to produce labeled and unlabeled oligomer fragments, wher the label is the same as that on the probe;

(c) separating any labeled cleaved oligomer fragments from labeled uncleaved oligomers, and (d) detecting the presence or absence of labeled oligomer fragments.

Where sufficient background signals exist in the hybridization step (a), after step (a) and before digestion step (b) there are included two additional steps: adding to the hybridization mixture of step (a) an unlabeled blocking oligomer complementary to each oligonucleotide probe except for at least one base pair mismatch at each restriction site being detected; and hybridizing the hybridization mixture in the presence of said blocking oligomer.

The specific oligonucleotide probe is chosen so as to span the informative restriction site of the nucleic acid sequence of interest, which is generally associated with a particular disease such as infectious or genetic diseases. The probe must be of sufficient length to achieve the desired proper specificity of hybridization to the nucleic acid. In the case of sickle cell anemia, oligonucleotide probes of about 40 bases in length have been found to be effective, although probes which are shorter or longer may also be utilized. The probe is labeled at one end is designed so that the restriction site of interest is nearer to that labeled end than to the unlabeled end. The label may include any suitable label known to those skilled in the art, including radioactive and non-radioactive labels. Typical radioactive labels include $^{32}P$, $^{125}I$, $^{35}S$ or the like. Non-radioactive labels include, for example, ligands such as biotin or thyroxine, as well as enzymes such as hydrolases or peroxidases, or the various chemiluminescers such as luciferin, or fluoroescent compounds like fluorescein and its derivatives. The probe may also be labeled at both ends with different types of labels for ease of separation, as, for example, by using an isotopic label at the end mentioned above and a boiotin label at the other end.

A preferred embodiment of the invention is a method for detecting the presence or absence of one or both alleles associated with a polymorphic restriction site in a specific nucleic acid sequence comprising the steps of:

(a) hybridizing said nucleic acid sequence with an oligonuclcoetide probe which is complementary to a region in said nucleic acid spanning a first restriction site present in only one allele and a second restriction site common to both alleles, and which probe is labeled at the end which is nearer to one of said restriction sites (and where there are sufficient background signals, adding to the hybridized mixture an unlabeled blocking oligomer complementary to said probe except for at least one base pair mismatch at said restriction site, and hybridizing again in the presence of the blocking oligomer);

(b) digesting said hybridized nucleic acid with a first restriction endonuclease which is capable of cleaving said probe only at said first restriction site so as to produce labeled and unlabeled oligomer fragments, where the label is the same as that on the probe;

(c) digesting said digest from step (b) with a second restriction endonuclease which is capable of cleaving said probe only at said second restriction site so as to produce labeled and unlabeled oligomer fragments, where the label is the same as that on the probe;

(d) separating any labeled cleaved oligomer fragments from uncleaved oligomers; and (e) detecting the presence or absence of labeled fragments of particular base lengths consistent with cleavage by the first or second restriction endonucleases.

Yet another embodiment of the invention relates to a diagnostic kit for the prenatal detection of sickle cell anemia comprising (a) a specific 40-base oligodeoxyribonucleotide probe complementary to normal β-globin ($β^A$) at the restriction site of interest which probe is labeled at the end nearer said restriction site, (b) restriction enzyme DdeI (and HinfI if sequential digestion is used), and optionally appropriate reference controls, means for detecting the labeled oligomers so formed, and, if necessary for detection, a specific blocking oligomer complementary to the probe. This kit results in a rapid yet sensitive assay for prenatal diagnosis of sickle cell anemia, which is greatly improved over the complex RFLP assay which requires sophisticated manipulation.

BRIEF DESCRIPTION OF THE DRAWINGS

FIG. 1 illustrates the sequence of a synthetic 40-base length oligodeoxyribonucleotide probe specific for the coding strand of normal β-globin (designated hereafter as HE09) and a complementary blocking oligomer (designated hereafter as HE10) used if necessary to minimize the non-specific hybridization of the labeled probe.

FIG. 2 illustrates the results obtained when the probe HE09 is hybridized to normal β-globin and to sickle cell β-globin containing the single base mismatch, each hybridization being followed by treatment with restriction enzyme DdeI.

FIG. 3 illustrates the comparison of normal β-globin, sickle cell β-globin, and normal δ-globin sequences indicating the restriction sites for DdeI and SfaNI resulting from single base differences.

FIG. 4 illustrates the effect of treating genomic DNA with restriction enzyme SfaNI prior to annealing the probe HE09.

FIG. 5 illustrates an autoradiograph indicating results obtained when cloned genes are treated with AluI or SfaNI prior to annealing to the probe HE09.

FIG. 7 illustrates a comparison of the probe HE09, which is matched to the beta-globin gene with one mismatch and is perfectly matched to the delta-globin gene, and probe HE11, which is perfectly matched to the beta-globin gene but has five mismatches with the delta-globin gene. HE09 anneals to the (+) strand of both genes, whereas HE11 anneals to the (−) strand of both genes. FIG. 7 also identifies the sequence of HE12, the blocking oligomer specific for HE11.

FIG. 8 also illustrates the region of δ-globin which hybridizes to GH11. GH11 exhibits some homology to the (+) strand of δ-globin, but the six mismatches which exist are sufficient to prevent any significant hybridization under the conditions employed in the reaction. In addition, FIG. 8 identifies the sequence of GH12, the blocking oligomer specific for GH11.

FIG. 9 illustrates an autoradiograph indicating results obtained when genomic DNA isolated from clinical samples is hybridized to probe HE11 and positive control GH11.

FIG. 10 illustrates the sequence of normal ($\beta^A$) and sickle cell ($\beta^S$) β-globin genes in the region of the DdeI site (single line) and HinfI site (double line).

FIG. 11 illustrates a comparison of probe HE11 with probe RS06, which is derived from HE11 by shifting the sequence five bases to span the HinfI site. The asterisk represents the radioactive tag at the 5' end of the molecule. FIG. 11 also indicates how RS06 anneals to the negative strand of the normal gene, reforming the HinfI site (double line) and the DdeI site (single line). In addition, FIG. 11 identifies the sequence of RS10, the blocking oligomer specific for RS06.

FIG. 12 illustrates the results obtained when probe RS06 is hybridized to normal β-globin followed by sequential digestion with DdeI and HinfI to produce a labeled octamer.

FIG. 13 illustrates the results obtained when probe RS06 is hybridized to sickle β-globin followed by sequential digestion with DdeI and HinfI to produce a labeled trimer.

FIG. 14 illustrates an autoradiograph indicating results obtained when genomic DNA isolated from cell lines and amplified using two oligodeoxyribonucleotide primers is hybridized to probe RS06 and sequentially digested with DdeI and HinfI, respectively.

DETAILED DESCRIPTION OF THE PREFERRED EMBODIMENTS

Figure 6:
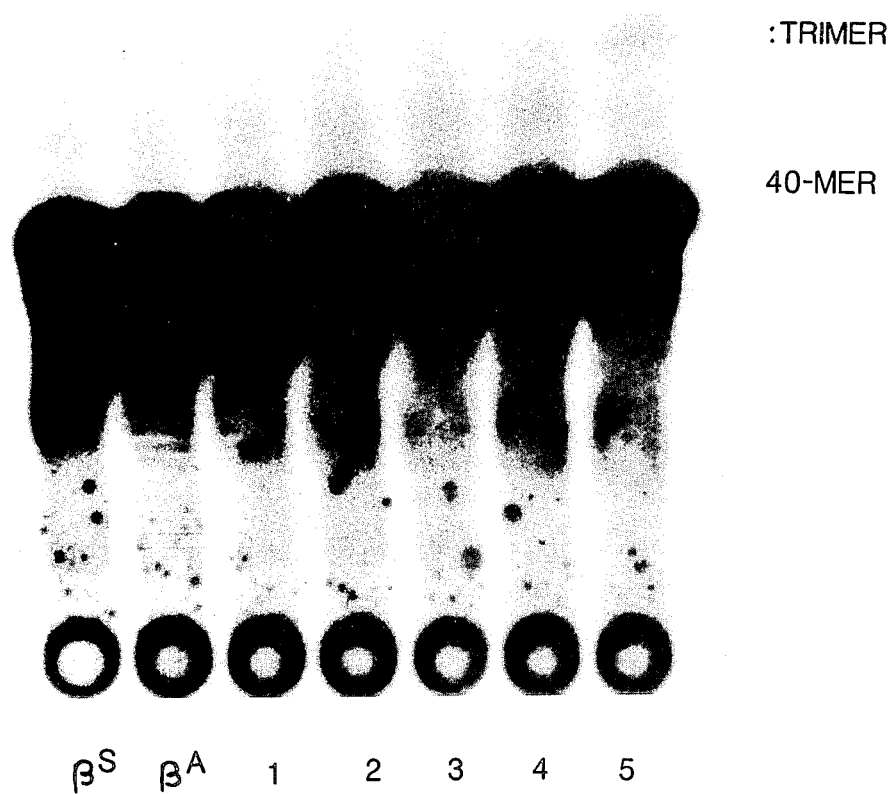
FIG. 6 illustrates an autoradiograph indicating results obtained when geomoic reconstructions of the normal β-globin gene at increasing copy numbers per diploid cell are hybridized to the probe HE09.

The term "oligonucleotide" as used herein in referring to probes, oligomer fragments to be detected, oligomer controls, unlabeled blocking oligomers and primers for amplification of sequences is defined as a molecule comprised of more than three deoxyribonucleotides or ribonucleotides. Its exact size will depend on many factors, which in turn depend on the ultimate function or use of the oligonucleotide.

As used herein, the terms "restriction endonucleases" and "restriction enzymes" refer to bacterial enzymes each of which cut double-stranded DNA at or near a specific nucleotide sequence.

As used herein, the term "DNA polymorphism" refers to the condition in which two or more different nucleotide sequences can exist at a particular site in DNA.

As used herein, the term "restriction fragment length polymorphism" ("RFLP") refers to the differences among individuals in the lengths of a particular restriction fragment.

As used herein, the term "sufficient background signals" refers to signals caused by occasional cross-hybridization of the oligonucleotide probe to non-specific genomic sequences and subsequent cleavage by the restriction endonuclease occurring at a frequency sufficient to interfere with the dectection of the correct signals.

The nucleic acid which may be employed herein may be derived from any source(s), including organisms, provided that it contain the particular restriction site or sites of interest within a given nucleic acid sequence. Thus, the process may employ pure DNA or RNA which is single or double stranded or a DNA-RNA hybrid or a mixture of nucleic acids, provided they can be cut by restriction endonucleases corresponding to the specific restriction site(s) of interest. Sources include, e.g., plasmids such as pBR322, cloned DNA or RNA, or genomic DNA or RNA from any source, including bacteria, yeasts, viruses, and higher organisms such as plants, birds, reptiles and mammals. Preferably the source is DNA, most preferably genomic DNA.

Genomic DNA may be prepared from blood, urine, tissue material such as chorionic villi or amniotic cells by a variety of techniques (such as that described by Maniatis, et al., *Molecular Cloning*, (1982) 280–281). If necessary or desired to lower the viscosity, the sample of prepared human DNA to be analyzed may be physically sheared or digested using a specific restriction endonuclease.

The nucleic acid may be used as is or the sequence it contains can be amplified to increase sensitivity as described hereafter in an example and as described in copending U.S. application Cetus Case 2177 to K. Mullis entitled "Process for Amplifying Nucleic Acid Sequences" filed concurrently herewith.

Once the nucleic acid of interest is ready for use, an oligonucleotide probe containing a region complementary to the restriction site(s) of interest is added, for each different restriction site present, preferably in molar excess. It is then allowed to anneal to its complementary sequence(s) in the nucleic acid. The end-labeled oligonucleotide probe used is designed to span the restriction site with the labeled end nearer to the restriction site of interest and to be of sufficient length to obtain specific hybridization under stringent conditions. The probe is preferably an oligodeoxyribonucleotide probe.

The use of the specific oligonucleotide probe which is annealed to the nucleic acid of interest varies significantly from the methods known in the art for oligomer hybridization. In the previously described methods, the DNA probes are added after the DNA has been digested by a restriction enzyme, size fractionated, and immobilized on a solid support such as an agarose gel or a filter membrane. In the present invention, the oligonucleotide probe has two functions: (1) to identify by solution hybridization the particular sequence of the nucleic acid of interest and (2) to act as the substrate for the restriction enzyme once it is annealed to the nucleic acid.

As discussed above, if there are sufficient background signals, after hybridization an unlabeled oligonucleotide (blocking oligomer) may be added to the reaction mixture which is specific for the probe utilized. This oligomer is complementary to the probe but has at least one base pair mismatch within each restriction site being detected, so that the labeled probe not already hybridized to the nucleic acid will hybridize to the blocking oligomer and therefore will not be cleaved by digestion with the restriction enzyme(s) recognizing each restriction site being detected. The function of the blocking oligomer is to eliminate the non-specific hybridization of any excess labeled probe to the non-polymorphic nucleic acid fragments under the conditions of reduced stringency necessary for the action of the subsequently added restriction enzyme. The number of base pair mismatches within each restriction site will depend mainly on the position of the restriction site within the probe.

After addition of the blocking oligomer, the reaction mixture is again subjected to hybridization conditions which are generally the same as those used in the first hybridization step, but usually for a shorter period of time. If a labeled positive control is present during the first hybridization step, it may be necessary to add an unlabeled blocking oligomer specific for the positive control, which unlabeled blocking oligomer contains at least one base pair mismatch within each restriction site being detected. The blocking oligomer will eliminate any excess labeled positive control. Such blocking oligomer can be added at the same time as the blocking oligomer for the probe.

Digestion of the duplex of oligonucleotide probe and nucleic acid with the appropriate restriction enzyme under suitable digestion conditions will cleave only those oligomers that have hybridized to the prepared nucleic acid and have reformed the restriction site. Since that site is near the labeled end of the oligonucleotide probe, the products of the digestion will include a very short piece of the labeled probe, provided the nucleic acid sequence is capable of being cleaved by the restriction enzyme being used.

The resulting mixture of labeled cut and uncut oligomers can be separated by any suitable separation technique, including addition of avidin to probes which are biotinylated on the other end, polyacrylamide gel electrophoresis and thin-layer chromatography. Analysis of the oligomer restriction products by thin-layer chromatography is useful for cloned genes. For genomic DNA, however, polyacrylamide gel electrophoresis, using, e.g., a 30% gel, is superior because it develops faster, has greater resolution sufficient to separate small oligomers visually, and is more sensitive with less background streaking of the intact probe so that less genomic DNA is necessary to create a detectable signal. The technique of adding avidin to a biotinylated probe having a different label on the end nearer the restriction site described above may also be very effective in separating the uncleaved probe from the labeled fragment(s).

Depending upon the type of label used for labeling the probe end nearer to the restriction site of interest, the separated fragments can then be detected by, for example, autoradiography, or other methods of detection such as fluorescence or chemiluminescence.

A practical application of this technique can be seen in its use for the detection of sickle cell anemia. Sickle cell anemia is a hemoglobin disease that is caused by a single base pair change, adenine to thymine, in the sixth codon of the $\beta$-globin gene. Normal $\beta$-globin ($\beta^A$) contains a restriction site for the restriction enzyme DdeI that spans the fifth and sixth codons. The general recognition sequence for DdeI is CTNAG, where N represents any nucleotide. For normal $\beta$-globin the specific sequence is CTGAG. In the case of sickle cell $\beta$-globin ($\beta^S$), the mutation changes the five base sequence to CTGTG which is no longer a cleavage site for DdeI. Thus, the DNA of the normal $\beta$-globin gene is cleaved in its fifth codon by DdeI but the same position in the sickle cell allele is not cut by the enzyme. It is to be noted that alternative restriction enzymes which serve the same purpose may be used in place of DdeI such as, e.g., MstII, CvnI or SauI.

A 40 base oligodeoxyribonucleotide probe (40-mer) (probe HE09) which is complementary to a region of the normal $\beta$-globin gene containing the polymorphic DdeI restriction site may be synthesized and labeled at its 5' end. The labeled probe may then be added to genomic DNA, preferably in molar excess, and allowed to anneal to its complementary sequence in the DNA. A positive and/or negative control may be present in the hybridization mixture if necessary to ensure meaningful results.

After the hybridization, an unlabeled 40 base length oligodeoxyribonucleotide (blocking oligomer) (HE10) complementary to the probe but with a mismatch within the DdeI site so that the labeled probe which hybridizes to the blocking oligomer will not be cleaved by DdeI digestion (FIG. 1) may be added to the reaction mixture. The mixture is then subjected to the same hybridization conditions for a lesser period of time.

The hybridization mixture is then digested with DdeI or an equivalent restriction enzyme. Following this treatment with the restriction enzyme, the cut and uncut labeled oligomers can be rapidly separated as described above and visualized by an appropriate technique.

FIG. 2 provides graphic examples of the resulting labeled oligomers when this type of analysis is performed on the normal $\beta$-globin and sickle cell $\beta$-globin genes. Normal $\beta$-globin, which retains the DdeI restriction site, is cleaved by the enzyme and results in the formation of a labeled trimer (3-mer), while the equivalent portion of the sickle cell $\beta$-globin gene is not cut by DdeI so that the probe remains intact.

Depending on the particular probe utilized, it may be necessary to treat the DNA of interest with the restriction enzyme SfaNI prior to its being annealed with the probe. This will be required when the probe cross-hybridizes to the $\delta$-globin gene of the human genome which always reforms the DdeI restriction site, as in the case of probe HE09. FIG. 3 shows the single base differences among normal $\beta$-globin, sickle cell $\beta$-globin and $\delta$-globin and their respective DdeI or SfaNI sites. For assurance that the resulting oligomers reflect the restriction site present only in the normal $\beta$-globin gene (to avoid false positive results), the DdeI site in $\delta$-globin must be removed if such a probe is used.

The enzyme SfaNI can be used to remove the DdeI site from $\delta$-globin. The SfaNI (GCATC) site is present at position 23–27 in $\delta$-globin but not in normal $\beta$-globin or sickle cell $\beta$-globin due to the difference at base 26 (FIG. 3). Since SfaNI cuts 5 and 9 bases "downstream" of its recognition site, the effect of SfaNI digestion is to remove the DdeI site. If the genomic DNA is digested with this enzyme before being annealed to the oligodeoxyribonucleotide probe which crossreacts with $\delta$-globin, the probe will be unable to reform the DdeI site with $\delta$-globin thereby assuring that the 3-mer formed in the process is due solely to the probe being annealed to normal $\beta$-globin. FIG. 4 provides a comparison among the three forms of globin after treatment with SfaNI indicating the lack of the DdeI site except for normal β-globin. Digestion with DdeI would, therefore, result in the formation of a 3-mer only with normal β-globin, confirming that the assay is definitive for detecting normal β-globin. In this manner patients who are normal ($\beta^A\beta^A$) or carriers of the sickle cell allele ($\beta^A\beta^S$) will be differentiated from patients having sickle cell anemia ($\beta^S\beta^S$).

In a preferred embodiment the probe does not cross-hybridize to the δ-globin gene so that predigestion of the genomic DNA with SfaNI to inactivate the δ-gene is not required. SfaNI is an expensive enzyme and is available only in dilute concentrations. An example of a probe which is specific for the β-globin gene but forms five mismatches with δ-globin is shown as HE11 in FIG. 7. It is compared to probe HE09 which hybridizes very well to both globin genes. The five mismatches are sufficiently destabilizing to prevent probe HE11 from hybridizing to the δ-globin gene. FIG. 7 also shows the relationship between HE11 and its specific blocking oligomer, designated HE12. The base pair mismatch is located within the DdeI site and prevents cleavage of the HE11/HE12 hybrid by that enzyme.

A labeled positive control oligonucleotide (oligomer) may be added to the hybridization mixture containing the probe to ensure that the lack of a signal is not due to an error in performing the test. For example, the β-globin gene contains several invariant (non-polymorphic) DdeI sites, which, unlike the polymorphic DdeI sites associated with sickle cell anemia, are always present in the β-globin gene. A positive control oligomer can be designed which anneals to the region surrounding one of these non-polymorphic DdeI sites and is labeled at the end nearer the non-polymorphic DdeI site. When it is added to the hybridization mixture, it serves as an internal positive control for the hybridization and digestion of the probe.

Figure 8:
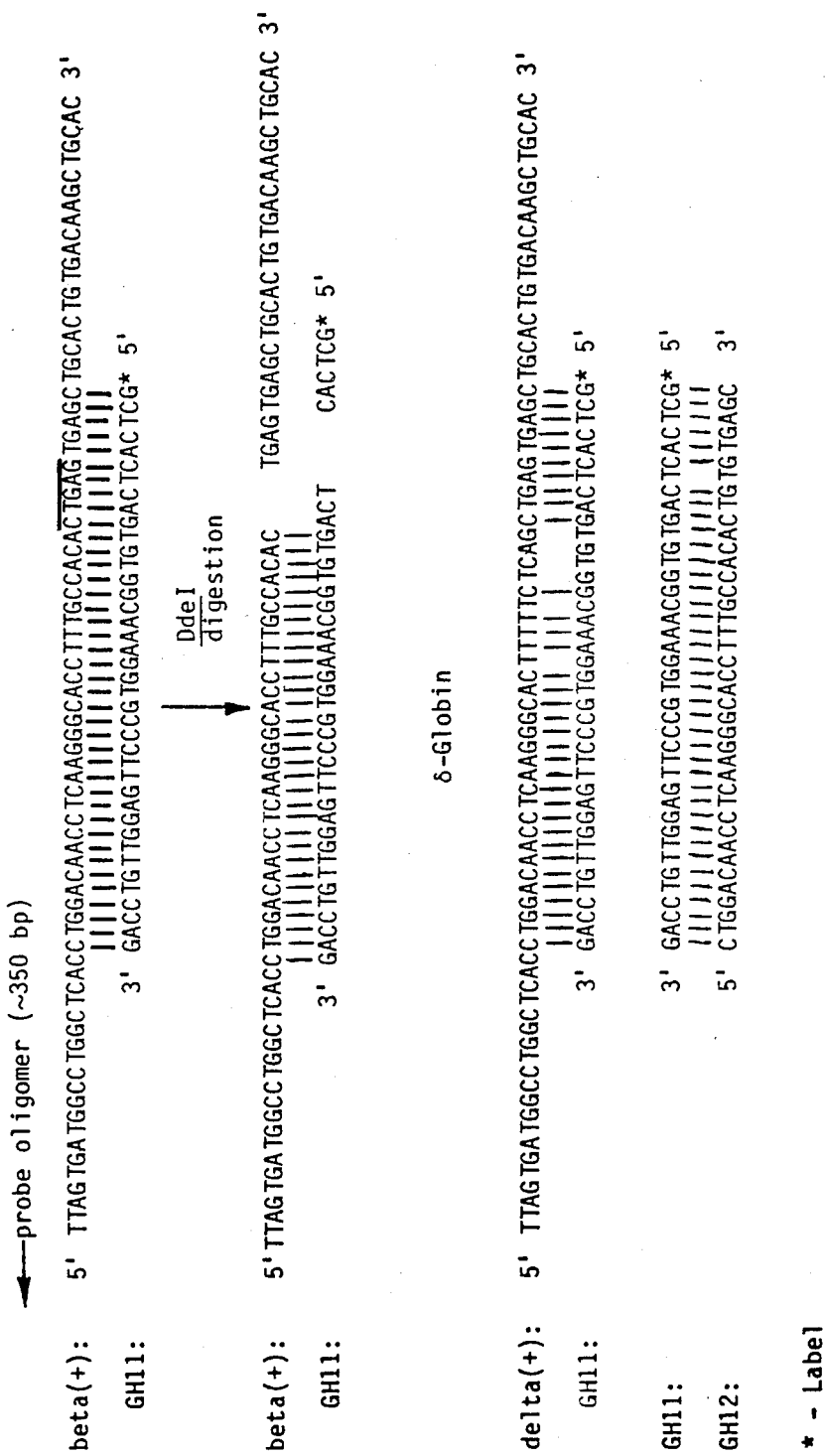
FIG. 8 illustrates the results obtained when a positive control oligonucleotide (GH11) is hybridized to normal β-globin followed by treatment with restriction enzyme DdeI to produce a labeled hexamer. The oligonucleotide GH11 anneals to the (+) strand of the β-globin gene approximately 350 bases downstream from the oligodeoxyribonucleotide probe HE11. The asterisk represents the radioactive tag at the 5'-end of the molecule and the bar indicates the invariant DdeI site CTGAG.

FIG. 8 illustrates a labeled 40-mer positive control, designated GH11, specific for probe HE11, which anneals to the (+) strand of the β-globin gene approximately 350 bases downstream from the probe HE11. Upon digestion of the annealing mixture of GH11 and β-globin with DdeI a labeled hexamer (6-mer) is generated. This positive control is specific for β-globin and, as shown in FIG. 8, does not significantly anneal to δ-globin due to six base pair mismatches. FIG. 8 also shows the relationship between GH11 and its specific blocking oligomer, designated GH12. The base pair mismatch is located within the DdeI site and prevents cleavage of the GH11/GH12 hybrid by that enzyme.

This positive control oligomer is particularly important for testing genomic DNA which could be homozygous for the sickle cell allele. If this were the case, the oligonucleotide probe will not be cleaved by DdeI because the probe cannot reform the DdeI site when it anneals to the sickle cell β-globin gene. Without a positive control, however, it is difficult to exclude the possibility that no signal is caused by an error in testing. The blocking oligomer for the positive control is added to the reaction mixture along with the blocking oligomer for the probe after hybridization of the probe with the DNA in the presence of the positive control. The function of such blocking oligomer is to eliminate any excess positive control present in the hybridization mixture.

In a most preferred embodiment, for detection of genetic diseases caused by a single base pair mutation in a sequence, a sequential digestion technique is used to determine directly and positively the nature of the alleles, i.e., whether the genotype is normal, mutant or carrier. The oligodeoxyribonucleotide probe HE11 mentioned above could directly detect the normal β-globin gene but not the sickle cell allele. This is because the trimer signal is generated only when the probe anneals to the normal gene and reforms the DdeI site. No oligomer cleavage product is produced when the HE11 probe hybridizes to the sickle cell sequence, so that the absence of a signal indicates the presence of the sickle cell gene. Consequently, the identification of the clinically significant sickle cell individual (SS) is made by the absence of any specific signal.

Furthermore, using the probe HE11 it is difficult to distinguish normal individuals (AA) from those who carry the sickle cell trait (AS), since a trimer signal is produced in each case. (In principle, the signal intensity of an AA individual should be twice that of an AS patient due to gene dosage. In practice, however, intensity differences are difficult to rely on unless very careful techniques are employed.)

A new method and probe, designated RS06, were developed to overcome these problems. The probe is capable of distinguishing between normal and sickle cell sequences by generating different signal fragments depending on the particular allele to which it is annealed—an octamer if RS06 anneals to the normal gene or a trimer if it binds to the sickle cell gene. This procedure relies on an invariant HinfI site in the β-globin gene which is immediately adjacent to the polymorphic DdeI site (FIG. 10). The 40-base RS06 probe, which is cloely related to probe HE11, spans both of these restriction sites (FIG. 11). FIG. 11 also shows the relationship between RS06 and its specific blocking oliogomer, RS10. The single base pair mismatch located within the HinfI site and the double mismatches within the DdeI site prevent cleavage of the RS06/RS10 hybrid by those enzymes.

In outline, the method involves annealing the labeled probe to the β-globin sequences and then digesting with DdeI. All RS06 molecules that have annealed to normal β-globin genes will reform the DdeI site and be cleaved by the enzyme, producing a labeled octamer (FIG. 12). Those probe molecules that hybridize to the sickle cell sequence do not reform the DdeI site and, of course, are not cut by that enzyme. With the subsequent addition of HinfI to the reaction, all oligomers that remain bound to the sickle cell gene will be restricted by HinfI and a labeled trimer will result (FIG. 13).

The probe RS06 does not require a labeled positive control nor a blocking oligomer for the control because the positive control is built into the probe.

On a stoichiometric basis, a normal individual (AA) will generate two octamers; a sickle cell carrier (AS), one octamer and one trimer; and a sickle cell individual (AA), two trimers. Thus, a specific signal is associated with the presence of the sickle cell allele and differentiation between AA and AS genotypes is now possible.

The method herein may also be used to detect the presence of specific invariant (nonpolymorphic) restriction sites in specific nucleic acid sequences associated with diseases such as infectious diseases. Examples of infectious diseases include those caused by bacterial organisms such as Salmonella, Chlamydia, gonorrhea, Legionella, etc.; viraL organisms such as hepatitis and RNA viruses; parasitic organisms such as malaria; and other related organisms. In addition, the method herein may be used to detect the absence of specific genes (e.g., α-globin) for the clinical diagnosis of α-thalassemia or the presence of 1-3 copies of α-globin, and the mutation or amplification of specific genes such as the conversion of proto-oncogenes to oncogenes. For example, the n-myc gene has been shown to be amplified in a variety of cancers.

The following examples are offered by way of illustration and are not intended to limit the invention in any manner. In these examples all percentages are by weight if for solids and by volume if for liquids and all temperatures are in degrees Celsius unless otherwise noted.

EXAMPLE I

Use of Cloned Genes to Illustrate the Principle of the Method for Detecting Polymorphic Restriction Sites Synthesis of Oligodeoxyribonucleotides Automated Synthesis Procedures: The diethylphosphoramidites, synthesized according to Beaucage and Caruthers (*Tetrahedron Letters* (1981) 22: 1859-1862), were sequentially condensed to a nucleoside derivatized controlled pore glass support using a Biosearch SAM-1. The procedure included detritylation with trichloroacetic acid in dichloromethane, condensation using benzotriazole as activating proton donor, and capping with acetic anhydride and dimethylaminopyridine in tetrahydrofuran and pyridine. Cycle time was approximately 30 minutes. Yields at each step were essentially quantitative and were determined by collection and spectroscopic examination of the dimethoxytrityl alcohol released during detritylation.

Oligodeoxyribonucleotide Deprotection and Purification Procedures: The solid support was removed from the column and exposed to 1 ml concentrated ammonium hydroxide at room temperature for four hours in a closed tube. The support was then removed by filtration and the solution containing the partially protected oligodeoxyribonucleotide was brought to 55° C. for five hours. Ammonia was removed and the residue was applied to a preparative polyacrylamide gel. Electrophoresis was carried out at 30 volts/cm for 90 minutes after which the band containing the product was identified by UV shadowing of a fluorescent plate. The band was excised and eluted with 1 ml distilled water overnight at 4° C. This solution was applied to an Altech RP18 column and eluted with a 7-13% gradient of acetonitrile in 1% ammonium acetate buffer at pH 6.0. The elution was monitored by UV absorbance at 260 nm and the appropriate fraction collected, quantitated by UV absorbance in a fixed volume and evaporated to dryness at room temperature in a vacuum centrifuge.

Characterization of Oligodeoxyribonucleotides: Test aliquots of the purified oligodeoxyribonucleotides were $^{32}P$ labeled with polynucleotide kinase and $\gamma$-$^{32}P$-ATP. The labeled compounds were examined by autoradiography of 14-20% polyacrylamide gels after electrophoresis for 45 minutes at 50 volts/cm. This procedure verifies the molecular weight. Base composition was determined by digestion of the oligodeoxyribonucleotide to nucleosides by use of venom diesterase and bacterial alkaline phosphatase and subsequent separation and quantitation of the derived nucleosides using a reversed phase HPLC column and a 10% acetonitrile, 1% ammonium acetate mobile phase.

Phosphorylation of Synthetic Oligodeoxyribonucleotide Probe

The synthetic oligodeoxyribonucleotide probe of 40 bases in length, in the amount of 10 pmole, was labeled at the 5'-end with two units of T4 polynucleotide kinase (New England Biolabs) and 50 pmole $\gamma$-$^{32}P$-ATP (New England Nuclear, ~3000 Ci/mmole) in a 40 μl reaction volume containing 70 mM Tris (pH 7.6), 100 mM NaCl, 10 mM MgCl$_2$, and 10 mM 2-mercaptoethanol for one hour at 37° C. The volume was then adjusted to 100 μl with Tris-EDTA (TE) buffer (10 mM Tris buffer, 0.1 mM EDTA, pH 8.0) and the oligomer separated from the unincorporated ATP by spin dialysis in a 1 ml Bio Gel P-4 column (Bio Rad) equilibrated with TE buffer. (Maniatis, et al., *Molecular Cloning* (1982) 464-465). TCA precipitation of the reaction products before and after spin dialysis indicated that 70-80% of the probe oligomers were labeled and that 70% of the applied material was recovered from the column. The concentration of the kinased oligodeoxyribonucleotide probe was adjusted to 20 pmole/ml with TE buffer.

Construction of Cloned Globin Genes

A 1.9 kb BamHI fragment of the normal β-globin gene was isolated from the cosmid pFC11 described by F. Collins et al., *PNAS*, 81, 4894-4898 (1984) and inserted into the BamHI site of pBR328 (Soberon, et al., *Gene* (1980) 9: 287-305). This fragment, which encompasses the region that hybridizes to the synthetic 40-mer probe, includes the first and second exons, first intron, and 5' flanking sequences of the gene (Lawn et al., *Cell* (1978) 15: 1157-1174). This clone was designated pBR328::β$^S$-1.9 (abbreviated to pBR:β$^S$). ATCC No. 39,618, deposited May 25, 1984.

The corresponding 1.9 kb BamHI fragment of the sickle cell allele of β-globin was isolated from the cosmid pFC12 described by F. Collins et al., supra, and cloned as above. This clone was designated pBR328::β$^2$-1.9 (abbreviated to pBR:β$^S$). ATCC No. 39,699 deposited May 25, 1984.

A similar 1.4 kb EcoRI/BamHI fragment of the normal δ-globin gene was isolated from pFC12 and cloned into the EcoRI/BamHI site of pBR328. This fragment spans the region of the δ-globin gene that cross-hybridizes to the probe and includes the first exon and 5' flanking sequences of the gene (Lawn et al., *Cell* (1978) 15: 1157-1174). This clone was designated pBR328::δ-1.4 (abbreviated to pBR:δ). ATCC No. 39,700 deposited May 25, 1984.

Each recombinant plasmid was transformed into and propagated in *E. coli* (ATCC No. 39,607).

Digestion of Cloned Globin Genes with AluI or SfaNI

Eight micrograms each of pBR:β$^A$, pBR:β$^S$, and pBR:δ were individually digested in a 100 μl volume with either 30 units of AluI (New England Biolabs) for 1.5 hours at 37° C. or 2.4 units of SfaNI (New England Biolabs) overnight at 37° C. in both cases using the buffer conditions recommended by the manufacturer. The digested DNA samples were ethanol precipitated and resuspended in TE buffer to a final concentration of 25 pmole/ml.

Hybridization and Digestion of Cloned Globin Genes and the Oligodeoxyribonucleotide Probe Ten microliters (0.25 pmole) each of AluI-digested or SfaNI-digested pBR:β$^A$, pBR:β$^S$, and pBR:δ were mixed with 5 μl kinased probe (0.10 pmole) and TE buffer to a final volume of 36 μl in a 1.5 ml Eppendorf Microfuge tube. The DNA was denatured by heating at 95° C. for 10 minutes in a heat block, spun briefly in a Microfuge to remove condensation from the cap of the tube, and returned to the heat block. Four microliters of 1.5M NaCl was added to the sample, mixed gently, and transferred to a fan-forced incubator set at 56° C. and allowed to anneal for three hours. A fan-forced incubator is preferred over a heat block or water bath to promote uniform heat distribution and avoid condensation during the hybridization period.

Four microliters of the unlabeled blocking oligomer HE10 (1.0 pmole), having the sequence: 5'-AACCT-CAAACAGACACCATGGTGGACCT-GACTCCTGTGGA-3' and prepared as described above, was then added and the hybridization was continued for an additional 30 minutes at the same temperature. Four microliters of 60 mM $MgCl_2$ and one microliter of DdeI (10 units, New England Biolabs) were added and the reannealed DNA was digested for 15 minutes at 56° C. The reaction was stopped by heating briefly at 95° C.

Ten microliters of each sample was applied to a precoated, glass-backed silica gel thin layer chromatography plate (M-N Sil G-25 UV254, Brinkmann Instruments), dried under a heat lamp, and developed overnight in a solvent composed of 45% n-propanol, 45% ammonium hydroxide, 10% water. The plate was then dried and autoradiographed with a single intensification screen overnight at −80° C.

Discussion of the Autoradiograph (FIG. 5)

Prior to the annealing with the 40-mer probe, the cloned genomic DNA for normal β-globin (pBR:$β^A$), sickle cell β-globin (pBR:$β^S$) and δ-globin (pBR:δ) was treated with the restriction enzyme AluI (30 units) which cuts the DNA into approximately the same size fragments as with treatment with restriction enzyme SfaNI. When annealed to the 40-mer probe followed by treatment with the restriction enzyme DdeI, the DdeI site is reformed in the normal β-globin and δ-globin genes resulting in the formation of the trimer band as shown in Lanes 1 and 3. Because sickle cell β-globin contains the point mutation preventing cleavage by DdeI, only a 40-mer band is seen in Lane 2 of the autoradiograph.

Lanes 4 through 6 represent the same clones as in Lanes 1 through 3; however, treatment is with the restriction enzyme SfaNI (2.4 units). The treatment with SfaNI removes the DdeI site from δ-globin which results in the formation of a trimer only when the normal β-globin gene is present. As shown in the autoradiograph, treatment with SfaNI results in the synthetic probe being unable to reform the DdeI site with δ-globin. Since this site is also missing in sickle cell β-globin, a band representative of the trimer will be formed only when the probe is annealed to normal β-globin.

EXAMPLE II

Use of genomic reconstructions to demonstrate the sensitivity of the method for detecting polymorphic restriction sites Synthesis and Phosphorylation of Oligodeoxyribonucleotides The end-labeled oligodeoxyribonucleotide probe and its complementary blocking oligomer were prepared as described in Example I except that the final concentration of the kinased probe was adjusted to 1 pmole/ml and the concentration of the blocking oligomer was 100 pmole/ml.

Digestion of Human Genomic DNA with DdeI

Human genomic DNA homozygous for normal β-globin was extracted from the lymphoid T cell line Molt4 (Human Genetic Mutant Cell Repository, (HMCR), GM2219C) using previously described methods (Stetler et al., Proc. Nat. Acad. Sci. (1982), 79: 5966–5970).

One hundred micrograms of human genomic DNA were digested with 60 units of DdeI (New England Biolabs) using the buffer conditions recommended by the manufacturer. After overnight incubation at 37° C, the DNA was ethanol precipitated, dried under vacuum, and resuspended in 100 μl of TE buffer.

Preparation of Genomic DNA Reconstructions

Based on a human haploid genome size of $3 \times 10^9$ base pairs, 20 μg of genomic DNA contains 10 tmole ($1 \times 10^5$ pmole) of the β-globin gene. This is equivalent to two copies per diploid cell.

To five 20 μg portions of DdeI-digested Molt4 DNA were added either 0 tmole, 5 tmole, 10 tmole, 20 tmole, or 40 tmole of BamHI-digested pBR:$β^A$ which represents zero, one, two, four, or eight copies of the β-globin gene per diploid cell, respectively. Final volumes of each were adjusted to 32 μl with TE buffer.

Hybridization of Genomic DNA Reconstructions with the Probe and Digestion Thereof The methods employed were essentially those described in Example I. Four microliters of kinased probe (0.004 pmole) was added to each 32 μl genomic reconstruction and denatured for 10 minutes at 95° C. in a heat block. The samples were spun briefly and returned to the heat block. Four microliters of 1.5M NaCl was added to each tube, mixed gently, and transferred to a fan-forced incubator at 56° C. and allowed to anneal overnight.

Four microliters of unlabeled blocking oligomer HE10 (0.4 pmole) was then added and the hybridization was continued for an additional 15 minutes at the same temperature. Four microliters of 60 mM $MgCl_2$ and one microliter of DdeI (10 units, New England Biolabs) were added and the reannealed DNA was digested for 15 minutes at 56° C. The reaction was stopped by heating briefly at 95° C.

Each sample was applied to a pre-coated, glass-backed silica gel thin layer chromatography plate (M-N sil G-25 UV254, Brinkmann Instruments) in four 12 μl serial applications, dried under a heat lamp, and developed overnight in a solvent composed of 45% n-propanol, 45% ammonium hydroxide, 10% water. The plate was then dried and autoradiographed with a single intensification screen for four days at −80° C.

Discussion of the Autoradiograph (FIG. 6)

Lanes 1 through 5 each contain 20 μg of Molt4 genomic DNA to which were added amounts of PBR:$β^A$ calculated to represent the genetic dosage if the β-globin gene were present at zero, one, two, four, and eight copies per diploid cell, respectively.

Digestion of the Molt4 DNA with DdeI prior to hybridization with the labeled probe renders that DNA unable to reform a DdeI site upon annealing to the probe and thus precludes the subsequent cleavage of that probe. This is demonstrated in Lane 1 where, in the absence of any exogenous pBR:$β^A$, no labeled trimer is observed.

Lane 2 represents the signal intensity expected if the normal β-globin gene is present at one copy per diploid cell and is equivalent to a heterozyous individual who carries the sickle-cell trait ($β^Aβ^S$).

Lane 3 represents the signal intensity expected if the normal β-globin gene is present at two copies per diploid cell and is equivalent to a normal homozygous individual ($\beta^A\beta^A$).

Lane 4 and Lane 5 are included for comparison purposes only to provide a relative means of comparing intensity of results. Normally individuals would not be found to possess either four or eight copies per diploid cell.

EXAMPLE III

Use of probe HE11 in genomic DNA

Synthesis and Phosphorylation of Oligodeoxyribonucleotides

The probe, HE11, and the blocking oligomer, HE12, shown in FIG. 7, were synthesized according to the procedures given in Example I. In addition, the positive control oligomer, GH11, and its associated blocking oligomer, GH12, as identified in FIG. 8, were synthesized by those same procedures.

Five pmole each of HE11 and GH11 (10 pmole total) were labeled together with four units of T4 polynucleotide kinase (New England Biolabs) and 50 pmole $\gamma$-$^{32}$P-ATP (New England Nuclear, about 7200 Ci/mmole) in a 40 μl reaction volume containing 70 mM Tris (pH 7.6), 10 mM MgCl$_2$, 1.5 mM spermine, and 2.5 mM dithiothreitol for 90 minutes at 37° C. The volume was then adjusted to 100 μl with 25 mM EDTA and purified over a P4 spin dialysis column as described in Example I. The labeled oligomers were further purified by electrophoresis on a 18% polyacrylamide gel (19:1 acrylamide:BIS, Bio Rad) in Tris-boric acid-EDTA (TBE) buffer (89 mM Tris, 89 mM boric acid, 2.5 mM EDTA, pH 8.3) for 500 vhr. After localization by autoradiography, the portion of the gel containing the labeled HE11/GH11 was excised, crushed, and eluted into 0.2 ml TE buffer overnight at 4° C. TCA precipitation of the reaction product indicated that the reaction was about 70% complete (5.1 Ci/mmole) and that 35% (3.5 pmole) of the kinased oligomers was recovered from the gel at a concentration of 17.5 pmole/ml (8.75 pmole/ml each).

The unlabeled HE12 and GH12 blocking oligomers were pooled and used at a concentration of 400 pmole/ml (200 pmole/ml each).

Isolation of Human Genomic DNA from Cell Lines

High molecular weight genomic DNA was isolated from the lymphoid cell lines Molt4, SC-1, and GM2064 using essentially the method of Maniatis (Maniatis et al., *Molecular Cloning*, (1982) 280-281).

Molt4 as described in Example II is a T cell line homozygous for normal $\beta$-globin, and SC-1, deposited with ATCC on Mar. 19, 1985, is an EBV-transformed B cell line homozygous for the sickle cell allele. GM2064 (HMCR, GM2064) was originally isolated from an individual homozygous for hereditary persistence of fetal hemoglobin (HPFH) and contains no beta- or delta-globin gene sequences. All cell lines were maintained in RPM1-1640 with 10% fetal calf serum.

Isolation of Human Genomic DNA from Clinical Blood Samples

Eight clinical blood samples (5-10 ml each) of known $\beta$-globin genotypes were obtained from Dr. Bertram Lubin of Children's Hospital in Oakland, Calif. They included normal homozygotes (AA), sickle cell carriers (AS), and sickle cell homozygotes (SS). To prevent experimental bias the samples were coded so that the genotypes were unknown. Genomic DNA was prepared from the buffy coat fraction, which is composed primarily of peripheral blood lymphocytes, using a modification of the procedure described by Nunberg et al., *Proc. Nat. Acad. Sci.*, 75: 5553-5556 (1978).

The cells were resuspended in 5 ml Tris-EDTA-NaCl (TEN) buffer (10 mM Tris pH 8, 1 mM EDTA, 10 mM NaCl) and adjusted to 0.2 mg/ml proteinase K, 0.5% SDS, and incubated overnight at 37° C. Sodium perchlorate was then added to 0.7M and the lysate gently shaken for 1-2 hours at room temperature. The lysate was extracted with 30 ml phenol/chloroform (1:1), then with 30 ml chloroform, and followed by ethanol precipitation of the nucleic acids. The pellet was resuspended in 2 ml TE buffer and RNase A added to 0.005 mg/ml. After digestion for one hour at 37+ C., the DNA was extracted once each with equal volumes of phenol, phenol/chloroform, and chloroform, and ethanol precipitated. The DNA was resuspended in 0.5 ml TE buffer and the concentration determined by absorbance at 260 nm.

Preparation of Genomic DNA Reconstructions

For comparison purposes, reconstructions involving the addition of calculated amounts of cloned normal $\beta$-globin gene sequences to genomic DNA were done as described in Example II to approximate the genetic dosage of one, two, four, and eight copies per cell, with the exception that uncut SC-1 DNA was used as carrier instead of DdeI-cut Molt4.

Hybridization/Digestion of Genomic DNA with Probes/DdeI

The methods employed were generally those described in Example I. Twenty micrograms of genomic DNA was dispensed into a 1.5 Microfuge tube and the final volume adjusted to 30 μl with TE buffer. A mineral oil cap (about 0.1 ml) was then overlayed to prevent evaporation and avoid the necessity of a fan-forced incubator. The genomic DNA was denatured by heating at 95° C. for 10 minutes. Ten microliters of 0.6M NaCl containing 0.04 pmole of labeled HE11/GH11 probe oligomers (0.02 pmole each) was added to the tube, mixed gently, and immediately transferred to a 56° C. heat block for three hours. Four microliters of unlabeled HE12/GH12 blocking oligomer (0.8 pmole each) was added and the hybridization continued for an additional 20 minutes at the same temperature. Five microliters of 60 mM MgCl$_2$ and 1 μl of DdeI (10 units, New England Biolabs) were added and the reannealed DNA was digested for 20 minutes at 56° C. The reaction was stopped by the addition of 4 μl 75 mM EDTA and 6 μl tracking dye to a final volume of 60 μl.

The mineral oil was extracted with 0.2 ml chloroform and 18 μl of the reaction (6 μg genomic DNA) was loaded onto a 30% polyacrylamide mini-gel (19:1, Bio Rad) in a Hoeffer SE200 apparatus. The gel was electrophoresed at 300 volts for one hour until the bromphenol blue dye front migrated to 30.0 cm off-origin. The top 1.5 cm of the gel, containing the intact 40-mer probes, was cut off and discarded to reduce the amount of background during subsequent autoradiography. The remaining gel was exposed for five days with two intensification screens at -70° C.

Discussion of Autoradiograph of Genomic DNA (FIG. 9)

Each lane contained 6 μg of genomic DNA. Lanes A, B and I-N contained the clinical samples designated CH1, CH2,, CH3, CH4, CH5, CH6, CH7 and CH8, respectively; Lanes C and O contained control DNA from the normal $\beta$-globin cell line Molt4 described above; Lanes D and P contained control DNA from the sickle cell β-globin cell line SC-1 described above; Lanes E-H are reconstructions containing SC-1 to which were added amounts of cloned normal β-globin gene to approximately one, two, four and eight copies per cell, respectively.

The Molt4 and SC-1 control lanes demonstrate the kind of signal expected in normal homozygotes (AA) and sickle cell homozygotes (SS). The clinical samples CH3, CH4, CH5, CH6, and CH8 clearly lacked any signal trimer and are predicted to be sickle cell homozygotes (SS). The presence of a strong trimer in both CH1 and CH2 indicates that these individuals are normal (AA), whereas the slightly fainter signal in CH7 suggests that this patient is a sickle cell carrier (AS).

EXAMPLE IV

Use of probe HE11 in cloned DNA

When probe HE11 was hybridized to the three cloned genes of Example I using the technique of this example and then digested, the 3-mer was produced only with normal β-globin and not with sickle cell β-globin or δ-globin, confirming that the probe was specific to normal β-globin.

EXAMPLE V

Sequential digestion of amplified genomic DNA

Synthesis and Phosphorylation of Oligodeoxyribonucleotides

The probe, RS06, and the blocking oligomer, RS10, shown in FIG. 11 were synthesized according to the procedures given in Example I. RS06 was labeled and purified essentially as described in Example III to a specific activity of 4.9 Ci/mmole and final concentration of 20 pmole/ml.

The unlabeled RS10 blocking oligomer was used at a concentration of 200 pmole/ml.

Isolation of Human Genomic DNA from Cell Lines

High molecular weight genomic DNA was isolated from the lymphoid cell lines Molt4, SC-1, and GM2064 as described in Example III.

Isolation of Human Genomic DNA from Clinical Blood Samples

A clinical sample designated CH12 from a known sickle cell carrier (AS) was obtained from Dr. Lubin (see Example III), and DNA was extracted therefrom as described in Example III.

Polymerase Chain Reaction to Amplify Selectively β-Globin Sequences

Two micrograms of each of the four genomic DNAs described above was placed in an initial 100 μl reaction volume containing 10 mM Tris buffer (pH 7.5), 50 mM NaCl, 10 mM MgCl₂, 150 pmole of Primer A of the sequence d(CACAGGGCACTAACG), and 150 pmole of Primer B of the sequence d(CTTTGCTTCTGACACA) and overlayed with about 100 μl mineral oil to prevent evaporation.

Each DNA sample underwent 15 cycles of amplification where one cycle is composed of three steps:

(1) Denature in a heat block set at 95° C. for two minutes.

(2) Transfer immediately to a heat block set at 30° C. for two minutes to allow primers and genomic DNA to anneal.

(3) Add 2 μl of a solution containing 5 units of the Klenow fragment of *E. coli* DNA polymerase I (New England Biolabs), 1 nmole each of dATP, dCTP, dGTP and TTP, in a buffer composed of 10 mM Tris (pH 7.5), 50 mM NaCl, 10 mM MgCl₂, and 4 mM dithiothreitol.

This extension reaction was allowed to proceed for 10 minutes at 30° C.

After the final cycle, the reaction was inactivated by heating at 95° C. for two minutes. The mineral oil was extracted with 0.2 ml of chloroform and discarded. The final reaction volume was 130 μl.

Hybridization/Digestion of Amplified Genomic DNA with Probes and DdeI/HinfI

The methods employed were generally those described in Example III. Forth-five microliters of the amplified genomic DNA was ethanol precipitated and resuspended in an equal volume of TE buffer. Ten microliters (containing the pre-amplification equivalent of 154 ng of genomic DNA) was dispensed into a 1.5 ml Microfuge tube and 20 μl of TE buffer to a final volume of 30 μl. The sample was overlayed with mineral oil and denatured at 95° C. for 10 minutes. Ten microliters of 0.6M NaCl containing 0.02 pmole of labeled RS06 probe was added to the tube, mixed gently, and immediately transferred to a 56° C. heat block for one hour. Four microliters of unlabeled RS10 blocking oligomer (0.8 pmole) was added and the hybridization continued for an additional 10 minutes at the same temperature. Five microliters of 60 mM MgCl₂/0.1% BSA and 1 μl of DdeI (10 units, New England Biolabs) were added and the reannealed DNA was digested for 30 minutes at 56° C. One microliter of HinfI (10 units, New England Biolabs) was then added and incubated for another 30 minutes. The reaction was stopped by the addition of 4 μl 75 mM EDTA and 6 μl tracking dye to a final volume of 61 μl.

The mineral oil was extracted with 0.2 ml chloroform, and 18 μl of the reaction mixture (45 ng genomic DNA) was loaded onto a 30% polyacrylamide mini-gel (19:1, Bio Rad) in a Hoeffer SE200 apparatus. The gel was electrophoresed at approximately 300 volts for one hour until the bromphenol blue dye front migrated to 3.0 cm off-origin. The top 1.5 cm of the gel was removed and the remaining gel was exposed for four days with one intensification screen at −70° C.

Discussion of Autoradiograph (FIG. 14)

Each lane contains 45 ng of amplified genomic DNA. Lane A contains Molt4 DNA; Lane B, CH12; Lane C, SC-1; and Lane D, GM2064. Molt4 represents the genotype of a normal individual with two copies of the $\beta^A$ gene per cell (AA), CH12 is a clinical sample from a sickle cell carrier with one $\beta^A$ and one $\beta^S$ gene per cell (AS), and SC-1 represents the genotype of a sickle cell individual whith two copies of the $\beta^S$ gene per cell (SS). GM2064, which contains no beta- or delta-globin sequences, is present as a negative control.

As seen in the autoradiogram, the DdeI-cleaved, $\beta^A$-specific octamer is present only in those DNA's containing the $\beta^A$ gene (Lanes A ane B), and the HinfI-cleaved, $\beta^S$-specific trimer is present only in those DNA's containing the $\beta^S$ gene (Lanes B and C). The presence of both trimer and octamer (Lane B) is diagnostic for a sickel cell carrier and is distinguishable from a normal individual (Lane A) with only octamer and a sickle cell afflicted individual (Lane C) with only trimer.

As a comparison, repeating the experiment described above using non-amplified genomic DNA revealed that the amplification increased the sensitivity of detection by at least 1000 fold.

An experiment was performed to detect the absence of a sequence in genomic DNA amplified as described in Example V using probe RS06, which contains the invariant HinfI site. The trimer HinfI cleavage product was detected if β-globin was present in the DNA but was not detected when β-globin was deleted.

The allele of β-globin encoding the $\beta^C$ chain cannot be distinguished from the $\beta^A$ allele by RFLP analysis because the nucleotide substitution that gives rise to the $\beta^C$ chain is in the N position of the DdeI (MstII, CvnI, SauI) recognition sequence CTNAG. Thus, the endonuclease cleaves both $\beta^A$ and $\beta^C$ alleles although the actual sequences within the restriction site are different. The specificity of the oligonucleotide restriction method herein is based on the ability of a mismatch within the restriction site to abolish or significantly inhibit cleavage. Therefore, an end-labeled oligonucleotide probe based on the $\beta^A$ sequence should be cleaved if it hybridizes to a $\beta^A$ genomic sequence but not to a $\beta^S$ or $\beta^C$ sequence. Conversely, an end-labeled oligonucleotide probe based on the $\beta^C$ sequence should be cleaved if it hybridizes to a $\beta^C$ genomic sequence but not to a $\beta^A$ or $\beta^S$. Thus, the oligomer restriction method herein allows for the detection of the $\beta^C$ allele and, thus, for the diagnosis of AC carriers and the clinically significant SC condition.

Deposit of Materials

The following clones and cell line were deposited with the American Type Culture Collection (ATCC), 12301 Parklawn Drive, Rockville, Md., 20852 USA.

| CELL LINE OR CLONE | CMCC# | DATE OF DEPOSIT | ATCC ACCESSION NO. |
|---|---|---|---|
| pBR:$\beta^A$ | 2036 | May 25, 1984 | 39,698 |
| pBR:$\beta^S$ | 2037 | May 25, 1984 | 39,699 |
| pBR:δ | 2038 | May 25, 1984 | 39,700 |
| SC-1 | 0082 | March 19, 1985 | — |
|  |  | CRL8756 |  |

The deposit of clones pBR:$\beta^A$, pBR:$\beta^S$ and pBR:δ and cell line SC-1 were made pursuant to a contract between the ATCC and the assignee of this patent application, Cetus Corporation. The contract with ATCC provides for permanent availability of the progeny of these clones and cell line to the public on the issuance of the U.S. patent describing and identifying the deposit or the publications or upon the laying open to the public of any U.S. or foreign patent application, whichever comes first, and for availability of the progeny of these clones and cell line to one determined by the U.S. Commissioner of Patents and Trademarks to be entitled thereto according to 35 CFR §122 and the Commissioner's rules pursuant thereto (including 37 CFR §1.14 with particular reference to 886 OG 638). The assignee of the present application has agreed that if the clones or cell line on deposit should die or be lost or destroyed when cultivated under suitable conditions, they will be promptly replaced on notification with a viable culture of the same clone or cell line.

In summary, the oligomer restriction method herein detects the presence or absence of a specific restriction site in a specific nucleic acid sequence defined by the sequence of a oligonucleotide probe. For detection of sickle cell anemia, the absence of a polymorphic restriction site is diagnostic. The inability to detect a specific restriction site which is not genetically polymorphic but is invariant is, thus, diagnostic of the absence of the sequence complementary to the probe. An example is the detection of the invariant HinfI site in the β-globin specific oligodeoxyribonucleotide probe RS06 by the presence of the trimer HinfI cleavage product derived from $\beta^A$ and $\beta^S$ genomic DNA but not from genomic DNA of a β-globin deletion. Thus, this approach could be used to detect the absence of specific genes (e.g., α-globin) for the clinical diagnosis of α-thalassemia (hydrops foetalis). Similarly, this approach could be used to detect the presence of a specific sequence, for example, a pathogen-specific DNA sequence present in a clinical sample for infectious disease diagnosis, e.g., Chlamydia and Salmonella.

What is claimed is:

1. A method for detecting the presence or absence of at least one specific restriction site in a specific nucleic acid sequence comprising the steps of:
    (a) hybridizing said nucleic acid sequence in solution with an oligonucleotide probe for each restriction site being detected which probe is complementary to a region in said nucleic acid sequence spanning the respective restriction site of the probe and which probe is labeled at the end which is nearer to said respective restriction site than the other end of the probe;
    (b) digesting said hybridized nucleic acid sequence with a restriction endonuclease for each restriction site being detected by each probe which is capable of cleaving its respective probe at said restriction site being detected so as to produce labeled and unlabeled oligomer fragments;
    (c) separating any labeled cleaved oligomer fragments from labeled uncleaved oligomers; and
    (d) detecting the presence or absence of labeled oligomer fragments.

2. A method according to claim 1 wherein after step (a) and before step (b) the method further comprises the steps of:
    (a') adding to the hybridization mixture from step (a) an unlabeled blocking oligomer complementary to each probe except for at least one base pair mismatch at each restriction site being detected; and
    (a") hybridizing said hybridization mixture in the presence of said blocking oligomer.

3. A method according to claim 1 wherein said probe is labeled with a radioactive isotope, biotin, and enzyme, a chemiluminescent compound, or a fluorescent compound.

4. A method according to claim 1 wherein step (c) is carried out by polyacrylamide gel electrophoresis and step (d) is carried out by autoradiography.

5. A method according to claim 1 wherein said restriction site is polymorphic and said hybridization step is carried out in the presence of an oligomer which anneals to a region of said nucleic acid sequence which region contains a nonpolymorphic restriction site for said restriction endonuclease.

6. A method according to claim 1 wherein said probe is labeled at one end with a label for separation reactive with another compound added to the mixture and at the other end with a label which is not detected by adding such compound.

7. A method according to claim 6 wherein said probe is labeled with a luminescent or fluorescent label at one end and is labeled with biotin as the label for separation at the other end.

8. A method according to claim 1 wherein said nucleic acid sequence is a DNA sequence and said probe is an oligodeoxyribonucleotide.

9. A method according to claim 8 wherein said nucleic acid sequence is contained in a genomic DNA obtained from a patient sample and said restriction site is known to be associated with a particular disease or disease state.

10. A method according to claim 9 wherein the disease is an infectious disease.

11. A method according to claim 9 wherein said restriction site is known to be present in normal β-globin but absent in sickle cell β-globin, and said restriction endonuclease is DdeI, MstII, CvnI or SauI.

12. A method according to claim 2 wherein said nucleic acid sequence is contained in a genomic DNA obtained from a patient sample, said probe is an oligodeoxyribonucleotide, and said restriction site is known to be present in normal β-globin but absent in sickel cell β-globin, and said restriction endonuclease is DdeI, MstII, CvnI or SauI.

13. A method according to claim 12 wherein said probe is of the sequence:

3'-TTGGAGTTTGTCTGTGGTACCACGT-GGACTGAGGACTCCT-5', said blocking oligomer is of the sequence:

5'-AACCTCAAACAGACACCATGGT-GCACCTGACTCCTGTGGA-3', and before the hybridization step the DNA is treated with restriction enzyme SfaNI.

14. A method according to claim 12 wherein saie probe is of the sequence:

5'-TCCTGAGGAGAAGTCTGCCGT-TACTGCCCTGTGGGGCAAG-3', said blocking oligomer is of the sequence:

3'-AGGTCTCCTCTTCAGACGGCAATGACG-GGACACCCCGTTC-5', said first hybridization step (a) takes place in the presence of an oligomer of the sequence:

3'-GACCTGTTGGAGTTCCCGT-GGAAACGGTGTGACTCACTCG-5', and said second hybridization step (a") takes place in the presence of an unlabeled blocking oligomer of the sequence:

5'-CTGGACAACCTCAAGGGCACCTTTG-CCACACTGTGTGAGC-3'.

15. A method for detecting the presence or absence of one or both alleles of a polymorphic restriction site in a specific nucleic acid sequence comprising the steps of:
(a) hybridizing said nucleic acid sequence in solution with an oligonucleotide probe which is complementary to a region in said nucleic acid sequence spanning a first restriction site present in only one allele and a second restriction site commonto both alleles, and which probe is labeled at the end which is nearer to one of said restriction sites than the other end of the probe;
(b) digesting said hybridized nucleic acid sequence with a first restriction endonuclease which is capable of cleaving said probe only at said first restriction site so as to produce labeled and unlabeled oligomer fragments;
(c) digesting the product of step (b) with a second restriction endonuclease which is capable of cleaving said probe only at said second restriction site so as to produce labeled and unlabeled oligomer fragments;
(d) separating any labeled cleaved oligomer fragments from uncleaved oligomers; and
(e) detecting the presence or absence of labeled fragments of particular base lengths which are formed on cleavage by the first and second restriction endonucleases.

16. A method according to claim 15 wherein after step (a) and before step (b) the method further comprises the steps of:
(a') adding to the hybridization mixture from step (a) an unlabeled blocking oligomer complementary to said probe except for at least one base pair mismatch at the first or second restriction site; and
(a") hybridizing said hybridization mixture in the presence of said blocking oligomer.

17. A method according to claim 16 wherein said nucleic acid sequence is derived from genomic DNA obtained from a patient sample and said polymorphic restriction site is known to be associated with a particular disease or disease state.

18. A method according to claim 17 wherein said disease is sickle cell anemia, said first restriction site is DdeI present in normal β-globin but absent in sickle cell β-globin, and said second restriction site is HinfI present in both normal and sickle cell β-globin.

19. A method according to claim 18 wherein said probe is of the sequence:

5'-CTGACTCCTGAGGAGAAGTCTGCCGT-TACTGCCCTGTGGG-3' and said blocking oligomer is of the sequence:

3'-GACAGAGGTCACCTCTTCAGACG-GCAATGACGGGACACCC-5'.

20. A kit for the rapid detection of the presence or absence of at least one specific restriction site in a specific nucleic acid sequence comprising:
(a) an oligonucleotide probe for each restriction site being detected, which probe is complementary to a region in said nucleic acid sequence spanning the respective restriction site of the probe and which probe is labeled at the end which is nearer to said respective restriction site than the other end; and
(b) a restriction endonuclease for each restriction site being detected by each probe which is capable of cleaving said probe at said restriction site.

21. A kit according to claim 20 further comprising an unlabeled blocking oligomer complementary to each probe except for at least one basic pair mismatch at said restriction site.

22. A kit according to claim 21 wherein said restriction site is polymorphic, which kit further comprises a second oligomer which anneals to a region of said nucleic acid sequence which region contains a non-polymorphic restriction site for said restriction endonuclease, and an unlabeled blocking oligomer complementary to said second oligomer except for at least one base pair mismatch at said restriction site.

23. A kit according to claim 20 further comprising a means to detect the label on the probe.

24. A kit for the rapid detection of sickle cell anemia according to claim 20 wherein said nucleic acid sequence is a DNA sequence, said restriction endonuclease is DdeI, MstII, CvnI or SauI, and said probe is an oligodeoxyribonucleotide.

25. A kit according to claim 20 for detecting the presence of a restriction site known to be associated with an infectious disease.

26. A kit for detecting the presence or absence of one or both alleles of a polymorphic restriction site in a specific DNA sequence comprising:
(a) an oligodeoxyribonucleotide probe which is complementary to a region in said DNA sequence spanning a first restriction site present in only one allele and a second restriction site common to both alleles and which probe is labeled at the end which is nearer to one of said restriction sites than the other end of the probe;
(b) a first restriction endonuclease which is capable of cleaving said probe only at said first restriction site; and
(c) a second restriction endonuclease which is capable of cleaving said probe only at said second restriction site.

27. A kit according to claim 26 further comprising an unlabeled blocking oligomer complementary to said probe except for at least one base pair mismatch at said restriction site.

28. A kit according to claim 27 wherein said polymorphic restriction site is known to be associated with sickle cell anemia, said first restriction site is DdeI present in normal $\beta$-globin but absent in sickle cell $\beta$-globin, and said second restriction site is HinfI present in both normal and sickle cell $\beta$-globin.

* * * * *